United States Patent [19]
Fett et al.

[11] Patent Number: 5,520,914
[45] Date of Patent: *May 28, 1996

[54] ANTIBODIES TO ANGIOGENIN: IMMUNOTHERAPEUTIC AGENTS

[75] Inventors: James W. Fett, Waltham; Bert L. Vallee, Brookline; Edward M. Alderman, Waltham, all of Mass.

[73] Assignee: President and Fellows of Harvard College, Boston, Mass.

[*] Notice: The term of this patent shall not extend beyond the expiration date of Pat. No. 4,853,219.

[21] Appl. No.: 377,666

[22] Filed: Jan. 24, 1995

Related U.S. Application Data

[63] Continuation of Ser. No. 90,908, Jul. 13, 1993, abandoned, which is a continuation of Ser. No. 459,729, Jan. 24, 1990, abandoned, which is a continuation of PCT/US88/02590, Aug. 5, 1988 published as WO89/00862, which is a continuation-in-part of Ser. No. 83,231, Aug. 6, 1987, Pat. No. 4,853,219.

[51] Int. Cl.$^6$ ................................................. A61K 39/395
[52] U.S. Cl. ..................... 424/158.1; 424/130.1; 424/139.1; 424/145.1; 435/7.23; 436/64; 530/387.1; 530/388.1; 530/388.2; 530/388.23; 530/388.24; 530/389.2
[58] Field of Search ............................ 530/387.1, 388.1, 530/388.15, 388.2, 388.23, 388.24, 388.7, 389.2, 389.6, 387.7, 388.8; 424/130.1, 139.1, 145.1, 152.1, 156.1, 158.1, 172.1; 435/7.23; 436/64

[56] References Cited

U.S. PATENT DOCUMENTS

| | | | |
|---|---|---|---|
| 4,529,590 | 7/1985 | LeVeen et al. | 424/520 |
| 4,727,137 | 2/1988 | Vallee et al. | 530/412 |
| 4,853,219 | 8/1989 | Alderman et al. | 530/387 |
| 4,900,673 | 2/1990 | Harper et al. | 435/240.2 |

OTHER PUBLICATIONS

Svet–Moldavskii, Biol Abs, 65, Abs 60267, (1978).
Maione, T. E., et al, Cancer Research, vol. 51, Apr. 15, 1991, pp. 2077–2083.
Osthoff et al., 1987, Biochem. Biophys. Res. Comm. 146: 945–952.
Fett et al., 1985, Biochemistry 24: 5480–5486.
Strydom et al., 1985, Biochemistry 24: 5486–5494.
Brown et al., 1980, The Lancet 1: 682–685.
Svet–Moldavskii, 1977, Vopr. onkol. (Leningrad) 23: 74–76 (in Russian with English translation attached).
Folkman, 1974, Cancer Res. 34: 2109–2113.

*Primary Examiner*—Toni R. Scheiner
*Assistant Examiner*—Yvonne Eyler
*Attorney, Agent, or Firm*—Banner & Allegretti, Ltd.

[57] ABSTRACT

This invention relates to the production of antibodies to angiogenin or to fragments thereof and to methods of inhibiting angiogenesis in mammals by administering to mammals such antibodies or Fab or F(ab')$_2$ fragments thereof so as to inhibit angiogenic activity. In addition, this invention relates to pharmaceutical compositions comprising therapeutically effective amounts of antibody that are immunologically reactive with angiogenin and which can be administered to inhibit angiogenesis.

6 Claims, No Drawings

ANTIBODIES TO ANGIOGENIN: IMMUNOTHERAPEUTIC AGENTS

This application is a continuation of application Ser. No. 08/090,908 filed Jul. 13, 1993, now abandoned, which is a continuation of application Ser. No. 07/459,729 filed Jan. 24, 1990, now abandoned, which is a continuation of PCT/US88/02590, filed Aug. 5, 1988, published as WO89/00862, which is a continuation-in-part of application Ser. No. 07/083,231 filed Aug. 6, 1987 (issued as U.S. Pat. No. 4,853,219).

BACKGROUND OF THE INVENTION

1. Field of the Invention

Angiogenesis is the process of increased vascularization in response to an angiogenesis factor. It occurs as a result of the endothelial cells in the existing blood vessels being stimulated into mitosis, thereby producing a new capillary network which advances towards its stimulus.

Solid tumors in situ are supported by an extensive vascular network which supplies the tumor with nutrients and eliminates its waste. This extensive vascular network is thought to develop from the host's normal and less extensive vascular network in response to the secretion of substances known as tumor angiogenesis factor.

Angiogenesis factors are not specific for tumors alone. Recently, an angiogenesis factor has been isolated from the joint fluid of patients suffering from the inflammatory disease, rheumatoid arthritis. This angiogenesis factor was isolated from the synovial fluid of the inflamed joint and was serologically identical with the tumor angiogenesis factor isolated from animals with experimental cancers. (Lancet 1, 682, Mar. 1980).

In addition, angiogenesis is associated with the pathological condition known as diabetic retinopathy and also with normal wound healing.

The present invention relates to antibodies specific for the human angiogenesis factor, angiogenin. The antibodies of the present invention bind to the human angiogenin molecule inhibiting its activity, thereby inhibiting angiogenesis. The antibodies of the present invention are useful agents for inhibiting angiogenesis in humans and other mammals such as in the treatment of tumors, diabetic retinopathy, inflammatory diseases, and disease states where angiogenesis is not desired.

2. Description of the Related Art

LeVeen, U.S. Pat. No. 4,529,590, describes a method for producing a bovine angiogenesis factor. LeVeen's method consists of inducing a prolonged inflammatory response in the cattle secondary to the injection of irritants into the body cavity of the animal. The angiogenic material which LeVeen isolated from fluid at the site of irritation was only partially characterized; it tested positive for angiogenic activity on chick chorioallantoic membrane and was capable of evolving an immune response in animals but is distinguished from angiogenin by having an isoelectric point low enough to allow chromatography on an anion exchanger, such as DEAE cellulose.

Vallee et al., U.S. patent application Ser. No. 778,387 filed Sep. 20, 1985, hereby incorporated by reference described purification and characterization of angiogenin, an angiogenic protein from human adenocarcinoma cell line HT-29. Angiogenin was also described in Fett et al., Biochemistry, Vol. 24, pp. 5480–5486, (1985).

The present invention relates to antibodies specific to human angiogenin, and to therapeutic compositions containing them as well as their use in inhibiting angiogenesis in mammals.

SUMMARY OF THE INVENTION

This invention relates to the production of monoclonal and polyclonal antibodies (herein referred to as antibody) immunologically reactive with angiogenin, in particular, angiogenin having the amino acid sequence in Formula 1 below. The antibodies can be raised by challenging mammals, e.g. mice or rabbits, either with angiogenin or with various fragments of angiogenin, prepared either by synthesis or by degradation of angiogenin itself. The fragments of angiogenin used each contains one or more epitopes, functional subunits, or active sites. Antibodies raised to such fragments may display less undesirable cross-reactivity with foreign proteins than do antibodies to whole angiogenin; consequently, antibodies to fragments of angiogenin may produce fewer undesirable side effects when used therapeutically than do antibodies to whole angiogenin. The antibodies raised to such fragments of angiogenin are immunologically reactive to whole angiogenin.

Formula I is as follows:

```
     1                                                              15
<Glu—Asp—Asn—Ser—Arg—Tyr—Thr—His—Phe—Leu—Thr—Gln—His—Tyr—Asp—

30
Ala—Lys—Pro—Gln—Gly—Arg—Asp—Asp—Arg—Tyr—Cys—Glu—Ser—Ile—Met—

45
Arg—Arg—Arg—Gly—Leu—Thr—Ser—Pro—Cys—Lys—Asp—Ile—Asn—Thr—Phe—

60
Ile—His—Gly—Asn—Lys—Arg—Ser—Ile—Lys—Ala—Ile—Cys—Glu—Asn—Lys—

75
Asn—Gly—Asn—Pro—His—Arg—Glu—Asn—Leu—Arg—Ile—Ser—Lys—Ser—Ser—

90
Phe—Gln—Val—Thr—Thr—Cys—Lys—Leu—His—Cly—Gly—Ser—Pro—Trp—Pro—

105
Pro—Cys—Gln—Tyr—Arg—Ala—Thr—Ala—Gly—Phe—Arg—Asn—Val—Val—Val—
```

-continued $$\text{Ala—Cys—Glu—Asn—Gly—Leu—Pro—Val—His—Leu—Asp—Gln—Ser—Ile—Phe—}^{120}$$

$$\overset{123}{\text{Arg—Arg—Pro—OH.}}$$

DETAILED DESCRIPTION

A. Production of Polyclonal Antibodies (a) Immunization: Antibodies to human tumor angiogenin or fragments thereof are produced in both rabbits and mice by injection with the appropriate immunogen preparation. Rabbits are immunized in one of three ways. They are immunized by subcutaneous injections with a suspension comprising purified angiogenin conjugated to affinity gel beads which are emulsified in 1 ml of complete or incomplete Freund's adjuvant just prior to use. Alternatively, the rabbits are injected subcutaneously with purified angiogenin and/or synthetic peptide derivatives, either conjugated to keyhole Limpet hemocyanin (KLH) or carrier-free, which is likewise emulsified in 1 ml of complete or incomplete Freund's adjuvant immediately prior to injection.

Similarly, the mice are immunized by injection with purified angiogenin or fragments thereof conjugated to affinity gel beads which are emulsified in complete Freund's adjuvant just prior to injection. However, unlike the rabbits, the mice are preferably injected with the immunogen in the peritoneal cavity. Mice are also immunized by subcutanous injection with purified angiogenin and/or synthetic peptide derivatives, either conjugated to KLH or carrier-free, which is emulsified in complete or incomplete Freund's adjuvant prior to injection.

(b) Purification of Polyclonial Antibodies: Pursuant to immunization at ten to sixteen day intervals, blood is collected from both rabbits and mice twelve to sixteen days following each injection and assayed for the presence of specified antibody by ELISA (enzyme linked immunosorbent assay.) Once antibodies are present in sera they are purified in a multistep process consisting of precipitation by saturated ammonium sulfate, resuspension in saline, dialysis against normal saline, affinity gel chromatography on Protein A-Sepharose, further dialysis against water, and then lyophilization. Rabbits and mice are then boosted monthly with the appropriate imunogen in incomplete Freund's adjuvant.

The resultant purified antibody preparations contain polyclonal antibodies raised to angiogenin or fragments thereof which are utilized in the therapeutic studies later described.

B. Production Of Monoclonal Antibodies (a) Immunization: Balb/c mice were immunized by subcutaneous or intraperitoneal injection of angiogenin or peptide derivatives of angiogenin in complete or incomplete Freund's adjuvant. Three days before the fusion, the mice were boosted with an intraperitoneal injection of angiogenin or peptide derivatives of angiogenin.

(b) Purification of Monoclonal Antibodies: The monoclonal antibodies are partially purified from either hybridoma-conditioned media or ascites in a multistage process. Hybridoma-conditioned media is clarified initially by filtration, preferably through glass fiber filters. Ascites is produced in Charles River nu/nu outbred mice.

The mice are primed with 1 ml of intraperitoneal injection of pristane followed 7 days later with an intraperitoneal injection of 1×10$^6$ hybridoma cells. Ascites fluid is collected from the mice 1 to 2 weeks later, centrifuged to remove cells and frozen for subsequent purification. Antibodies in the filtered hybridoma-conditioned media or ascites are precipitated by saturated ammonium sulfate, centrifuged to a pellet, decanted, resuspended in saturated ammonium sulfate, pelleted again, resuspended in normal saline (0.15M NACl, pH 7.4) and finally dialyzed against normal saline (0.15M NaCl, pH 7.4). The resulting solution is purified further by Protein A-Sepharose chromatography, dialyzed against normal saline, sterile filtered and stored in aliquots at −70° C.

(c) Characterization of Monoclonal Antibodies: Monoclonal antibodies were characterized by ELISA and radioimmunoassay (RIA) for their ability to recognize other species of angiogenin such as bovine, porcine, and rabbit-derived angiogenin. In addition, mutants of angiogenin produced in our laboratory was used to characterize further the epitope binding of the monoclonal antibodies. One set of mutants consisted of single amino acids substitutions: the lysine at residue 40 substituted with either glutomine (K40Q) or arginine (K40R), the arginine with residue 66 substituted with alanine (R66A), tryptophan at residue 89 substituted with methionine (W89M), and the aspartic acid at residue 116 substituted with histidine (D116H) or alanine (D116A). The other set of mutants employed consisted of angiogenin-bovine RNase A hybrids (ARH): ARH in which angiogenin residues 58–70 are replaced with RNase residues 59–73 (ARH-1), ARH in which angiogenin residues 38–41 are replaced with RNase residues 38–42, (ARH-2), ARH in which ARH-1 is further substituted with angiogenin residues 8–22 replaced with RNase A residues 7–21 (ARH-3) and ARH in which angiogenin residues 8–22 are replaced with RNase A residues 7–21 (ARH-4).

C. Efficacy Of The Antibodies

Secondary to their ability to react immunologically with angiogenin, the antibodies of this invention possess anti-tumor activity in mammals. In particular, the antibodies of this invention prevented and inhibited tumor growth in mice as determined by immunoprophylactic and immunotherapeutic studies.

Similarly, Fab and F(ab')$_2$ fragments of antibodies to angiogenin should produce an analogous therapeutic effect since it is well known in the art that the Fab or F(ab')$_2$ fragments of an antibody possess the antibody binding site and are capable of binding to the antigen as avidly as the intact antibody.

Thus, the immunotherapeutic agents of this invention are monoclonal and polyclonal antibodies, Fab and F(ab')$_2$ fragments thereof, and mixtures thereof which are immunologically reactive with angiogenin and/or with natural and/or synthetic peptide fragments of angiogenin. These immunotherapeutic agents are useful medicaments in the treatment of pathological processes in mammals where angiogenesis is an undesired manifestation of the process.

Because these immunotherapeutic agents can inhibit angiogenesis, they are particularly useful in the treatment of tumors in mammals.

As pharmaceutical compositions, the immunotherapeutic agents of this invention can be administered in a wide variety of dosage forms, either alone or in combination with other pharmaceutically compatible medicaments, and in the form of pharmaceutical compositions suited for systemic or localized injection, time release implants and the like.

Typically, the immunotherapeutic agents of this invention are administered in the form of pharmaceutical compositions suited for injection consisting essentially of the free antibody and a pharmaceutical carrier.

The pharmaceutical carrier can either be a solid or semi-solid material, or a liquid in which the immunotherapeutic agent is dissolved, dispersed or suspended and which can optionally contain small amounts of pH buffering agents and/or preservatives. Suitable buffering agents include for example sodium acetate and pharmaceutical phosphate salts and the like. Pharmaceutically acceptable preservatives include for example benzyl alcohol and the like.

Representative of pharmaceutically effective dosage ranges are 6.6 µg to 66 µg of antibody/dose. However, therapeutically effective dosage ranges can be expected to vary based upon the avidity of the particular antibody selected, the size, age and weight of the patient being treated, and the like, and can readily be determined by simple experiment.

DESCRIPTION OF THE PREFERRED EMBODIMENTS

The following examples are given by way of illustration only and are not to be construed as limiting this invention either in spirit or in scope, as many modifications in materials and methods will be apparent from this disclosure to those skilled in the art.

EXAMPLE 1

Male NZW rabbits weighing 3–5 kg upon arrival were obtained from Milbrook Farms, Mass. and maintained according to AAALAS guidelines.

Inbred Balb/c (Balb/CAnNCr1BR) mice used for immunization to provide spleen cells for hybridoma-producing fusions are purchased from Charles River Laboratories' VAF+ (virus antibody free) facilities. Nude mice used for the tumor experiments as well as ascites production are also purchased from Charles River Laboratories. All mice are kept in autoclaved filter top cages in laminar flow, HEPA-filtered racks and are handled only by gloved and gowned personnel.

EXAMPLE 2

Rabbit Polyclonal Antibody

Preparations of angiogenin were conjugated to an affinity gel, AffiGel 10 (BioRad Laboratories, Burlingame, Calif.), according to manufacturer's instructions, at concentrations of 5 µg (total protein)/ml settled beads. Unreacted sites on the beads were blocked using 1M ethanolamine and the beads were then extensively washed with coupling buffer, then sterile distilled water. Fifty µl of 10% conjugated bead suspension was emulsified in 1 ml complete (or incomplete) Freund's adjuvant immediately prior to injection.

Alternatively, purified angiogenin and synthetic peptide derivatives were conjugated via glutaraldehyde to keyhold Limpet hemocyanin (KLH) at ratios of 50 µg/mg KLH. The resulting solution was to 5 mg (total protein)/ml sterile distilled water. Fifty µl (135 µg) KLH-conjugated angiogenin or peptide solution was emulsified in 1 ml complete (or incomplete) Freund's adjuvant immediately prior to injection.

All rabbits were injection subcutaneously at 10 day intervals dorsally, proceeding caudad. Adjuvant was alternated between complete and incomplete Freund's. Sera was collected from rabbits by venipuncture of the marginal ear vein 5 days following each injection, and assayed for the presence of specific antibody by ELISA (enzyme linked immunosorbant assays).

In addition, antibodies were also produced in rabbits by immunization with carrier-free angiogenin or synthetic peptide derivatives of angiogenin. Rabbits were initially injected subcutaneously with angiogenin (50 µg) emulsified in complete Freund's adjuvant. Two subsequent injections were given at two week intervals of angiogenin (50 µg) in incomplete Freund's adjuvant. Sera was collected by venipuncture of the marginal ear vein 14 days after the third injection and tested for the presence of specific angiogenin-binding antibodies by ELISA (enzyme-linked immunosorbent assay). The rabbits continued to be injected once per month with 50 µg of angiogenin in incomplete Freund's adjuvant, with sera taken by venipuncture of the marginal ear vein 12 to 14 days after each injection.

Immunoglobulins were precipitated from sera by the dropwise addition of equal volumes of saturated ammonium sulfate. The resulting suspension was stirred for 1 hr. at room temperature, then centrifuged at 10,000 g. Pelleted material was washed with saturated ammonium sulfate, then resuspended in minimal volume of 0.15M.NaCl, pH 7.4 (normal saline), loaded into 6000–8000 MW cutoff dialysis tubing, and dialyzed against normal saline. The dialyzed Ig fraction was then applied to a 5 ml bed of Protein A-Sepharose (Pharmacia Fine Chemicals, Piscataway, N.J.), and washed with normal saline. Specifically bound immunoglobulins were eluted from the column in 0.2M glycine-HCl, pH 3.5. These fractions were neutralized by immediate collection into 0.1 volume of 1M Tris-Cl, pH 8.0, pooled, and dialyzed as above. The dialyzed material was applied to a 20 ml bed of DEAE-cellulose and the leading fractions (unbound) were collected, pooled, dialyzed against distilled water, then lyophilized.

EXAMPLE 3

Mouse Monoclonal Antibody to Angiogenin

Balb/c mice were initially injected with 30 µg of angiogenin in complete Freund's adjuvant subcutaneously. Two more injections of 30 µg of angiogenin in incomplete Freund's adjuvant were given 10 days and 17 days after the initial injection. Three days before the fusion, mice were boosted with 30 µg of angiogenin in normal saline given as intraperitoneal injection.

On the day of the fusion, the mouse boosted with the angiogenin in saline was sacrificed and the spleen harvested. A suspension of spleen cells was obtained by purging the spleen with serum-free medium using a 22 gauge needle. The spleen cells were washed three times with 10 ml/wash of serum-free media. The Sp2/0 or P3x63-Ag 8.653 fusion partner myeloma cells to be used were also washed three times with serum-free medium. The spleen cells were mixed with the myeloma cells at a 4:1 spleen to myeloma cell ratio. The spleen-myeloma cell mixture was pelleted by centrifugation and placed in a water bath at 37° C. One ml of filtered polyethylene glycol (PEG, 0.83 mg/ml in serum-free media) was added slowly over a 30 second interval. After gentle mixing of the cells and PEG for 90 seconds, 5 ml of serum-free media was added over a 5 minute period followed by 14 ml of HAT media over a 1 minute period. The cells were then centrifuged for 7 minutes and the supernatant discarded. The cells were suspended in HAT media containing mouse peritoneal exudate cells ($4 \times 10^5$ cells/plate) and plated into 96-well tissue culture plates at 200 µl per well. Seven days after the fusion the HAT medium was removed and replaced with HT medium. Wells were checked daily for colony growth. Supernatants from those wells exhibiting colony growth were assayed for angiogenin-binding antibodies by ELISA. Cells yielding supernatant containing angiogenin-binding antibodies were subcloned twice by limiting dilution.

Partial purification

Hybridoma-conditioned medium or ascites fluid was clarified by filtration through Whatman glass fiber filters. Equal volumes of saturated ammonium sulfate were added dropwise to the clarified hybridoma-conditioned medium and stirred for 1 hr. at room temperature. The mixture was centrifuged (10,000 g) for 10 minutes and the resulting pellet resuspended in saturated ammonium sulfate and washed by centrifugation. Pelleted material was resuspended in normal saline and dialyzed as above against normal saline.

Purification

Clarified hybridoma-conditioned medium or ascites fluid was dialyzed overnight at 4° C. in 6000–8000 MW cutoff bags against 50 volumes 0.1M sodium phosphate buffer, pH 8.0. This material was applied to a 5 ml bed of Protein A-Sepharose. Unbound material was washed from the column using 0.1M sodium phosphate buffer, pH 8.0, and Ig enriched fraction eluted from the column in 0.1M sodium citrate buffer, pH 3.5, and dialyzed against normal saline. The resultant fraction was highly purified, as evidenced by gel electrophoresis under reducing conditions which revealed as major bands only the light and heavy chains of immunoglobulins.

EXAMPLE 4

Characterization of 26-2F monoclonal antibody

The monoclonal antibody 26-2F (ATCC [American Type Culture Collection, 12301 Parklawn Drive, Rockville, Md., 20852] Deposit Number HB9766) was the result of the fusion of the spleen cells of an angiogenin-immunized Balb/c mouse with the P3x63-Ag8.653 myeloma line. This monoclonal antibody is an IgGlk. It binds strongly to angiogenin both in a solid phase ELISA and a soluble phase (RIA). It does not bind to bovine, porcine, or rabbit angiogenin in a soluble phase inhibition assay for binding to iodinated angiogenin. In this same assay, 26-2F binds equally well to the D116A mutant as to native angiogenin and the binding to K40Q and K40R is only decreased by approximately two fold. In examining the interaction of the RNase-sequence containing mutants, 26-2F binds equally well to the ARH-1, ARH-3 and ARH-4 mutants as to the native angiogenin. However, in the inhibition RIA, 26-2F does not recognize the ARH-2 mutant.

EXAMPLE 5

Mouse Monoclonal Antibody to Synthetic Peptide 36–46

Balb/c mice were also injected with 50 μg of a synthetic peptide corresponding to residues 36–46 of angiogenin in complete Freund's adjuvant intraperitoneally. Two more injections of 50 μg of 36–46 in incomplete Freund's adjuvant were given at one month intervals after the initial injections followed by a boost with angiogenin (15 μg) in Freund's incomplete adjuvant after one month and three days before the fusion.

The fusion of immune spleen cells with the Sp2/0 mouse myeloma cells was performed essentially as described above. Wells were examined for colony growth and supernatants from those wells exhibiting growth were assayed for angiogenin-binding antibodies by radioimmunoassay. Cells producing angiogenin-binding antibodies were subcloned by limiting dilution.

EXAMPLE 6

Characterization of 51C9

The monoclonal antibody 51C9 (ATCC deposit number HB9767) was the result of the fusion of the spleen cells from a Balb/c mouse immunized with synthetic peptide 36–46 with the Sp2/0 myeloma line. The specificity of this antibody was determined using a competition assay where various competitors competed with $^{125}$I-angiogenin for binding to 51C9. The competitors are peptide-BEA conjugates, angiogenin mutants, angiogenin from different species or RNase A. Scatchard analysis as well as inverse Michaelis-Menten plots indicates a KD=$2.6 \times 10^{-9}$M. The following mutants react equally well with native human angiogenin: R66A, angiogenin clipped at positions 2 and 67, D116A, D116H, and ARH-1 which contains the fourth disulfide bridge of RNase A. 51C9 reacts with peptides 36-46-BSA, 41-51-BSA, 81-91-BSA but not with 1-21-BSA. Additionally, the antibody does not recognize porcine or bovine angiogenin or RNase A and reacts poorly with rabbit angiogenin and mutants K40Q, K40R, and W89M.

In summary, 51C9 recognizes an area on angiogenin spanning two discontinuous regions. Residue 89 is recognized since mutating this tryptophan to methionine reduces the affinity 30-fold. Residue 40 is also recognized since mutating this lysine to glutamine or arginine reduces the affinity 22-fold. Residue 37 is also a critical residue. When this residue is changed to arginine, as in the porcine and bovine angiogenin, 51C9 does not have much affinity. Since both porcine and bovine have Lys-40 and bovine angiogenin does not have Trp-89, the change of serine 37 to arginine might result in a 100-fold reduction in affinity. Finally, since 51C9 recognized 41-51-BSA, at least one of these residues is seen. Upon analysis of the 3-D model, residues 89, 37, and 40 reside in close proximity to each other. In addition, residues 90, 38, 39 and 41 might make contact with 51C9. The antibody binding pocket measures 34×12×7 angstroms or 7.9×2.8×1.6 amino acids. This more than accommodates these seven residues. According to the accessibility model of Haber and Novotny, as applied to angiogenin in a manner similar to that for renin (Evin et al., *Biochemistry*, 1988, 27, 156–164), these two regions are predicted as strongly antigenic. In fact, residues 89 and 38 are predicted to be the most accessible of all these residues.

Additionally, 51C9 does not recognize a complex formed by angiogenin and placental ribonuclease inhibitor (PRI). This implies that 51C9 and PRI recognize overlapping regions on the angiogenin molecule.

EXAMPLE 7

Immunotherapeutic Protocol

In these studies, male nude mice (5–7 weeks old) were kept at 2–4 mice per cage. Experimental groups of 10 mice were randomized by cages prior to experimentation. In addition the order of injection of the control and experimental preparations was varied from each experiment and the person injecting the tumor cell preparation was not knowledgeable as to the nature of the material mixed with the cells.

For monoclonal antibody therapy the experimental mice were injected with $1\times10^6$ HT-29 cells mixed with the antibody to be tested in phosphate-buffered saline (PBS) on day zero. The cells were incubated with antibody and PBS for 5 minutes prior to injection, and the injection of a group of 10 mice was then completed within an additional 5 minutes. Examination of the viability of the cells after such manipulation shows no significant change. The injection was given subcutaneously behind the left shoulder and the area of injection was demarcated with a VWR marking pen. Injections of the antibody and/or PBS were given daily for 14 days. Injections were given in the area previously marked until a tumor was noted, at which time the injection was moved to the visible tumor area if the tumor was outside the marked area. Tumor size was monitored using a caliper and measurements were given in cubic mm (length×width× depth). Presence of a tumor too small to measure was indicated as a "1". Body weight and photographic records were taken 2–3 times during the course of each experiment.

In the first two experiments, 88-06 and 88-07, two doses of the ammonium-sulfate-precipitated and protein A-Sepharose-chromatographed, ascites-derived 26-2F monoclonal antibody were given and compared with the PBS control. In the second set of experiments, 88-08 and 88-09, two sets of 10 mice each were given the lower dose of 26-2F and compared with the PBS control group as well as a set of mice given a subclass-matched nonspecific monoclonal, MOPC21 (Organon Teknika Corp., West Chester, Pa.).

Table 1, attached hereto, summarizes the results of the four experiments. Depicted are the percent of animals with tumors smaller than the smallest PBS (control) tumor as well as the percent of animals with no detectable tumor for days 7, 14, and 24. As compared with PBS and MOPC treatment, 26-2F administration decreases effectively tumor size in a high percentage of animals and protects completely against tumor development in several animals for at least one month after the last antibody injection.

In a test group of mice receiving polyclonal antibody, doses of antibody prepared against angiogenin-KLH (50 μg, 25 μg) were given two days prior to HT-29 cell administration ($5\times10^5$ cells) and on days 1, 4, 6, 8, 11 following tumor cell implantation. Likewise, PBS was administered as a "sham" treatment. The data in Table 2 illustrate the therapeutic effect of the polyclonal antibody. The results indicate that antibody treatment leads to decreased tumor growth in all groups and that several animals are protected completely from tumor development, i.e. zero tumor size. Optimal dosages of antibody can be determined by simple experimentation.

TABLE 2

| | Polyclonal Antibody Therapy | | | |
|---|---|---|---|---|
| Treatment | Mouse Number | Day 4 | Day 8 | Tumor Size (mm³) Day 13 |
| PBS (Control) | 1 | 1 | 30 | 300 |
| | 2 | 1 | 27 | 245 |
| | 3 | 1 | 8 | 125 |
| | 4 | 1 | 27 | 200 |
| | 5 | 1 | 4 | 175 |
| | 6 | 1 | 1 | 48 |
| | 7 | 1 | 8 | 80 |
| | 8 | 1 | 1 | 27 |
| | 9 | 1 | 27 | 175 |
| | 0 | 1 | 4 | 125 |
| | Mean | 1 | 14 | 150 |
| Antibody 50, μg | 11 | 0 | 0 | 2 |
| | 12 | 0 | 0 | 175 |
| | 13 | 0 | 0 | 1 |
| | 14 | 0 | 0 | 0 |
| | 15 | 0 | 0 | 0 |
| | 16 | 1 | 1 | 125 |
| | 17 | 1 | 0 | 9 |
| | 18 | 1 | 8 | 64 |
| | 19 | 1 | 27 | 120 |
| | 20 | 0 | 4 | 80 |
| | Mean | 0 | 4 | 58 |
| Antibody, 25 μg | 21 | 0 | 27 | 125 |
| | 22 | 1 | 0 | 8 |
| | 23 | 1 | 27 | 48 |
| | 24 | 1 | 27 | 100 |
| | 25 | 0 | 0 | 0 |
| | 26 | 1 | 27 | 125 |
| | 27 | 0 | 1 | 27 |
| | 28 | 0 | 1 | 27 |
| | 29 | 0 | 1 | 1 |
| | 30 | 1 | 0 | 0 |
| | Mean | 0 | 11 | 46 |

EXAMPLE 8

Generation of Antibodies to Angiogenin Using Peptide Fragments

Synthetic polypeptides were prepared corresponding to the amino acid sequences of Formula I: 6–21, 108–121, and 15–26. In each case, the polypeptide corresponding to the specified fragment of angiogenin was prepared by solid phase Merrifield synthesis on a polymer bead, then liberated with hydrofluoric acid and purified by high performance liquid chromatography, procedures which are all well known. See Barany and Merrifield, Peptides, Vol. 2, Special Methods in Peptide Synthesis, Part A, p. 3, Ed. Gross and Meinhofer, Academic Press N.Y. (1980) and Merrifield, Adv. Enzymology, Vol. 33, 221–296 (1969).

Each such synthetic peptide fragment was coupled to KLH with glutaraldehyde by conventional procedures, and the products were dialyzed against physiological saline.

The dialyzed products were used to immunize rabbits monthly subcutaneously with 100 mg peptide equivalents of the peptide/KLH mixtures employing, alternately, complete and incomplete Freund's adjuvant according to standard protocols. Blood samples were drawn monthly.

From each blood sample IgG was isolated from the immune serum by ammonium sulfate precipitation, Protein A-Sepharose chromatography, and DEAE ion-exchange chromatography to provide purified antibody.

Immunoreactivity of each antibody toward the peptide fragment and toward native whole angiogenin was assessed by enzyme-linked immunosorbent assay (ELISA). It was found that all three were immunoreactive to whole angiogenin. Other synthetic peptides have been prepared corresponding to fragments 30–41, 36–46, 48–61, and 108–123 of Formula I and are being used as immunogens.

TABLE 1

| | Monoclonal Antibody Therapy | | | | | | | | | | | |
|---|---|---|---|---|---|---|---|---|---|---|---|---|
| | Day 7 | | | | Day 14 | | | | Day 24 | | | |
| | PBS | MOPC 6.6 μg | 26-2F 66 μg | 26-2F 6.6 μg | PBS | MOPC 6.6 μg | 26-2F 66 μg | 26-2F 6.6 μg | PBS | MOPC 6.6 μg | 26-2F 66 μg | 26-2F 6.6 μg |
| <SM Control[a] | 0 | 11 | 50 | 55 | 0 | 0 | 45 | 55 | 0 | 0 | 50 | 45 |
| "0"[b] | 0 | 0 | 30 | 17 | 0 | 0 | 15 | 10 | 0 | 0 | 10 | 8 |
| n[c] | 40 | 20 | 20 | 60 | 40 | 20 | 20 | 60 | 30 | 10 | 20 | 40 |

[a]Percent of animals with tumors smaller than smallest PBS (control).
[b]Percent of animals with no detectable tumor.
[c]Total animals per group.

What is claimed is:

1. An antibody immunologically reactive to angiogenin or a fragment of angiogenin, wherein said antibody inhibits the angiogenic activity of angiogenin to inhibit the ability of circulating tumor cells to establish a vascularized tumor mass.

2. A monoclonal antibody immunologically reactive to an angiogenin antigen having the amino acid sequence of Formula I or a fragment of the sequence of Formula I, wherein said monoclonal antibody inhibits the angiogenic activity of angiogenin to inhibit the ability of circulating tumor cells to establish a vascularized tumor mass.

3. A pharmaceutical composition comprising an antibody according to claim 1 in a pharmaceutical carrier in an amount effective to inhibit the angiogenic activity of angiogenin.

4. A pharmaceutical composition comprising an antibody according to claim 2 in a pharmaceutically acceptable carrier in an amount effective to inhibit the angiogenic activity of angiogenin.

5. A method for inhibiting the angiogenic activity of angiogenin comprising administering an antibody according to claim 1 or a Fab or F(ab')$_2$ fragment thereof, in an amount sufficient to inhibit the ability of circulating tumor cells to establish a vascularized tumor mass.

6. A method of inhibiting the angiogenic activity of angiogenin comprising administering an antibody according to claim 2 or a Fab or F(ab')$_2$ fragment thereof, in an amount sufficient to inhibit the ability of circulating tumor cells to establish a vascularized tumor mass.

* * * * *